United States Patent
Thomas et al.

(10) Patent No.: US 10,441,212 B2
(45) Date of Patent: Oct. 15, 2019

(54) METHOD TO DETERMINE POSITIONS AND STATES OF AN ACTIVITY MONITORING DEVICE

(71) Applicant: WITHINGS, Issy les Moulineaux (FR)

(72) Inventors: Remi Thomas, Vanves (FR); Nadine Buard, Meudon (FR); Eric Carreel, Meudon (FR)

(73) Assignee: WITHINGS, Issy les Moulineaux (FR)

( * ) Notice: Subject to any disclaimer, the term of this patent is extended or adjusted under 35 U.S.C. 154(b) by 80 days.

(21) Appl. No.: 14/251,239

(22) Filed: Apr. 11, 2014

(65) Prior Publication Data
US 2015/0289802 A1 Oct. 15, 2015

(51) Int. Cl.
| | |
|---|---|
| *A61B 5/00* | (2006.01) |
| *G01P 15/02* | (2013.01) |
| *A61B 5/01* | (2006.01) |
| *A61B 5/11* | (2006.01) |
| *G06F 19/00* | (2018.01) |
| *G16H 40/63* | (2018.01) |

(52) U.S. Cl.
CPC ............. *A61B 5/4809* (2013.01); *A61B 5/01* (2013.01); *A61B 5/1118* (2013.01); *A61B 5/1123* (2013.01); *A61B 5/681* (2013.01); *G01P 15/02* (2013.01); *G06F 19/3481* (2013.01); *G16H 40/63* (2018.01); *A61B 2562/0219* (2013.01)

(58) Field of Classification Search
CPC .......... G06K 9/00335; A63B 2220/836; A63B 24/0062
See application file for complete search history.

(56) References Cited

U.S. PATENT DOCUMENTS

| | | | |
|---|---|---|---|
| 2008/0190202 A1 | 8/2008 | Kulach et al. | |
| 2010/0100004 A1* | 4/2010 | van Someren | 600/549 |
| 2010/0210975 A1* | 8/2010 | Anthony et al. | 600/595 |
| 2015/0031964 A1* | 1/2015 | Bly et al. | 600/301 |

FOREIGN PATENT DOCUMENTS

EP 2255209 12/2010

* cited by examiner

*Primary Examiner* — Scott Luan
(74) *Attorney, Agent, or Firm* — Miller, Matthias & Hull LLP (57) ABSTRACT

A method to determine a position and a state of a personal activity monitor worn by a user, such personal activity monitor comprising a motion sensor formed as an at least 3-axis accelerometer and a processor unit, the method comprising the steps of determining a number of changes of predominant axis per time period, and comparing it with exceeds a first predetermined threshold in order to infer a wrist worn condition, the method comprising the steps of determining a current level of activity and a temperature criterion to infer that the personal activity monitor is actually worn by the user and that the user has entered a sleep phase, or to infer that the user has emerged from sleep.

14 Claims, 5 Drawing Sheets

METHOD TO DETERMINE POSITIONS AND STATES OF AN ACTIVITY MONITORING DEVICE

FIELD OF THE DISCLOSURE

The present invention concerns activity monitors, in particular personal activity monitors intended to be coupled to a user in order to track or record the activity of the user.

BACKGROUND OF THE DISCLOSURE

More precisely, the present invention relates to a personal activity monitor (also called 'activity monitoring device' or 'personal activity tracker' or the like), that can be worn by its user on various positions, for example at the wrist, or at the waist, or in various other locations where it can be coupled to the user's body. More specifically, the present invention relates to a device having small dimensions and low weight, and which can be associated to the user's body via various coupling means, for instance associated to the wrist via a wrist strap, or associated to the waist via a belt clip and a belt, or associated to the chest via a clip on a shirt, or simply carried in a pocket of a cloth. Advantageously to the benefit of the user, a single device can be associated to the user's body in different manners using various attachments or coupling means; it is thus very flexible and convenient for the user who can wear the device nearly at all times regardless of the type of activity (bath/shower/swimming/sleeping not excluded). Nonetheless, the configuration when the user does not wear the device can sometimes occur and has to be contemplated.

Also the purpose of this monitoring device is to follow all the activities of the user as much as possible, various active physical activities, user's rest conditions, including user's sleep condition.

It is therefore required for the activity monitoring device to recognize both the current position of the device on the body, and also recognizes the type of activity undertaken by the user.

EP-A-2255209 discloses such a personal activity monitoring device. However, the method to identify the current device position relies on the one hand on complicated signal signatures and on the other hand does not consider rest and sleep activities.

Therefore, it arose a need to be able to identify more easily the current device position, in particular the wrist position and also to identify a user's sleep state, condition that has to be distinguished from a case when the device is not worn by the user.

SUMMARY OF THE DISCLOSURE

According to a first aspect of the present invention, it is disclosed a method to determine a position of a personal activity monitor (1) worn by a user (U), such personal activity monitor comprising a motion sensor (7) formed as an at least 3-axis accelerometer (X,Y,Z) and a processor unit (14),
the method comprising the steps of:
Wa—identify at each instant which axis (X,Y,Z) senses the largest acceleration,
Wb—determine a change of predominant axis when the largest acceleration change from one axis to another,
Wc—determine a number of changes of predominant axis per time period (Nbch),
Wd—define a wrist worn condition (WWC), meaning that the personal activity monitor is worn at the wrist of the user, and, if the number of changes of predominant axis per time period exceeds a first predetermined threshold (CW1), infer that the wrist worn condition is true.

Thereby, such method to determine that a personal activity monitor is worn at the wrist of the user turns out to be quite simple, does not require complex look-up table or algorithms.

In various embodiments of the first aspect of the invention, one may possibly have recourse in addition to one and/or other of the following arrangements.

In the course of step Wa—, the 3 linear acceleration signals are filtered by a low pass filter, such that the largest acceleration is provided by gravity; Thereby a simple and robust solution is provided to detect the absolute orientation of the monitoring device.

The method may comprise a further step We—, in which it is inferred that wrist worn condition is/become false, if the number of changes of predominant axis per time period (Nbch) is below a second predetermined threshold (CW2); Therefore, the monitoring device can recognize that the monitoring device is not worn anymore at the wrist, for example is worn at another position coupled to the user's body, or even not worn at all by the user.

The second predetermined threshold (CW2) is lower than the first predetermined threshold (CW1). Thereby a hysteresis is provided so that the decision on the wrist worn condition is made on positive conditions and chattering is avoided.

The number of changes of predominant axis is computed periodically over the last elapsed period. Therefore, the period can be chosen so that the wrist worn condition is determined substantially in a real time fashion.

The method may further comprise the use of a temperature sensor enclosed in the personal activity monitor, and in step Wd—, the wrist worn condition is maintained over a certain period of time (TTB) if a sensed temperature sensed by the temperature sensor meets a first predetermined temperature criterion (TPC1) over said certain period of time (TTB). Therefore, the wrist worn condition is extended even if the user does not move much for a certain time.

The first predetermined temperature criterion (TPC1) may be a temperature interval comprised between a first predefined temperature threshold (Tbody1) and a second predefined temperature threshold (Tbody2). This substantially corresponds to a temperature close to the skin temperature and is this turns out to be a simple and reliable criterion.

According to a second aspect of the present invention, it is disclosed a method to detect a sleep stat of a user (U) wearing a personal activity monitor (1), said personal activity monitor comprising a motion sensor (7), a processor unit (14) and a temperature sensor (4), the method comprising the steps of:
Sa—determine via the motion sensor a current sensed level of activity (AL), and compare this current level of activity to a predefined low level of activity (LAL),
Sb—determine via the temperature sensor a current temperature (STemp) at the vicinity of the activity monitor, and a first temperature profile (TPR1),
Sc—if the sensed level of activity is below the predefined low level of activity (LAL) for at least a first period of time (TT1) and if concurrently the first temperature profile meets a first predetermined temperature criterion (TPC1) over the first period of time (TT1) or over a second period of time (TT2), then infer that the personal activity monitor is actually worn by the user and that the user in a sleep state.

Thereby, such method allows the device to reliably determine the user's effective sleep.

According to a variant of the second aspect of the present invention, it is disclosed a method to detect a sleep phase of a user (U) wearing a personal activity monitor (1), said personal activity monitor comprising a motion sensor (7), a processor unit (14) and a temperature sensor (4), the method comprising the steps of:

Sa—determine via the motion sensor a current level of activity (AL), and compare this current level of activity to a predefined low level of activity, Sb—determine via the temperature sensor a current temperature at the vicinity of the activity monitor, and a first temperature profile (TPR1), Sc—if the sensed level of activity is below the predefined low level of activity (LAL) for at least a first period of time (TT1) and if concurrently the first temperature profile meets a first predetermined temperature criterion (TPC1) over the first period of time (TT1) or over a second period of time (TI2), then infer that the personal activity monitor is actually worn by the user and that the user has entered a sleep phase, Sd—if the sensed level of activity meets a wake activity criterion, infer that the user has emerged from sleep, Se—calculate the sleep duration of the user, between instants of entering and emerging from sleep.

Thereby, such method to determine the conditions "falling asleep" and "emerging from sleep" allows the device to reliably determine the duration of the user's effective sleep; this method further excludes period of time when the device is at rest but not worn by the user.

In various embodiments of the second aspect of the invention, one may possibly have recourse in addition to one and/or other of the following arrangements.

In the course of step Sd—, the wake activity criterion comprises at least a condition of the sensed level of activity being above the predefined low level of activity (LAL) for at least a third period of time (T3), or a condition of the sensed level of activity being above a second level of activity (MAL) for at least a fourth period of time (TT4). Thereby various conditions on activity level allow to reliably detect the awakening of the user.

The wake activity criterion may comprise at least a condition when the sensed temperature meets a second predetermined temperature criterion (TPC2), preferably the sensed temperature (Temp) is below a first predefined temperature threshold (Tbody1). Thereby a temperature condition is also defined to exit the sleeping state, this may useful in case the user put the monitoring device on a table just after awakening.

The processing unit may further calculate a ratio of change of sensed temperature per time unit (TCR), and the wake activity criterion may also comprise a condition in which said ratio of change of sensed temperature per time unit exceeds a predefined temperature change threshold (TCR0). Thus an additional condition is defined on change ratio of the sensed temperature.

The first predetermined temperature criterion (TPC1) is a temperature interval comprised between a first predefined temperature threshold (Tbody1) and a second predefined temperature threshold (Tbody2). This substantially corresponds to a temperature close to the skin temperature and is a simple and reliable criterion.

The motion sensor is formed as a 3-axis accelerometer (X,Y,Z) and the current sensed level of activity (AL) is determined by summing the average signals of the AC components of each 3 linear accelerometers. Thereby, this calculation provides an appropriate metric, faithfully reflecting the actual activity level of the user.

According to a third aspect of the present invention, it is disclosed a method to determine a coupling position of the monitoring device on the user's body among a plurality of possible body coupling positions, using the accelerometer signals, the method comprising the steps of collecting the accelerometer signals, analysing time and frequency characteristics of the collected signals, comparing said characteristics to predefined patterns, and then deciding the most likely current body coupling position. Preferably, the plurality of possible body coupling positions includes extremities (hand, wrist, foot), upper arm, upper leg, hip, waist, torso, neck, head. The predefined patterns may include criteria or thresholds on the following items: predominant spectrum frequency, frequency of orientation changes, amplitude, symmetry or the symmetry versus average value, etc.

According to a variant of the third aspect of the present invention, it is disclosed a method to determine on the one hand a coupling position of the monitoring device on the user's body among a plurality of possible body coupling positions and to concurrently determine on the other hand the type of activity undertaken by the user among a plurality of possible activities, using the accelerometer signals and the temperature signal, the method comprising the steps of collecting the accelerometer signals, analysing time and frequency characteristics of the collected signals, comparing said characteristics to predefined patterns, and then deciding the most likely current body coupling position and the most likely current user activity. The plurality of possible user's activities may include sleeping, walking, running, cycling, swimming, golfing, doing racket sport, etc. .

The predefined patterns may include criteria or thresholds on the following items regarding on the one hand acceleration signals: predominant frequency, frequency of orientation changes, amplitude, symmetry or the symmetry versus average value, etc, and the other hand predefined temperature thresholds regarding temperature signal.

According to a fourth aspect of the present invention, it is disclosed a method to correlate data from various external devices in order to make the decision on the current body coupling position and/or on the user current activity faster and more reliable. Said various external devices may include an air quality sensor ($CO_2$ or VOC sensor), a sleep sensor, a geo-location sensor, an image/video apparatus, a weighing scale with user detection, etc.

According to a further, fifth aspect of the present invention, it is disclosed a method to determine that the user is awake with a very low level of activity. Advantageously, this allows to distinguish a sleep state of the user from a very low active but still awake state.

BRIEF DESCRIPTION OF THE DRAWINGS

Other features and advantages of the invention appear from the following detailed description of one of its embodiments, given by way of non-limiting example, and with reference to the accompanying drawings.

On the drawings.

DETAILED DESCRIPTION OF THE DISCLOSURE

In the figures, the same references denote identical or similar elements.

Figure 1:
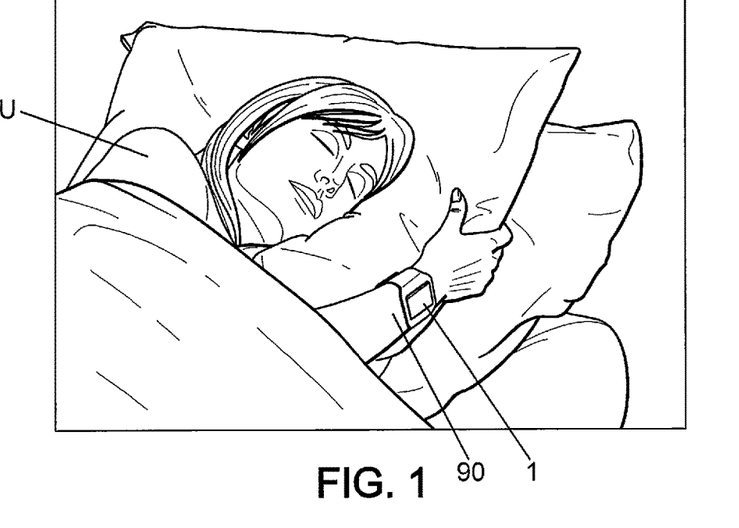
FIG. 1 is a schematic view of a user sleeping with a monitoring device at the wrist.

FIG. 1 shows a user U wearing an activity monitoring device 1 coupled to the body of the user. The illustrated activity monitor 1 may be formed as a small box, comprising a display system, to show the user activity. The activity monitor is able to inform the user on his activity, as walking, running, sleeping, stair climbing, etc. . .

The illustrated activity monitor 1 exhibits a weight below 10 grams, preferentially below 8 grams. Its size is also particularly small, the thickness being less than 8 mm, the length being less than 43 mm, the height being less than 22 mm, it is particularly easy and discreet to wear. The activity monitor 1 may be the product "Pulse"™ from the applicant Withings. Alternatively, the activity monitor 1 may be integrated in various other devices like a watch like "Smartwatch"™, eye glasses, or glasses like "Google glasses"™, in a headset, in a hearing aid or in an instrumented necklace.

Figure 2:
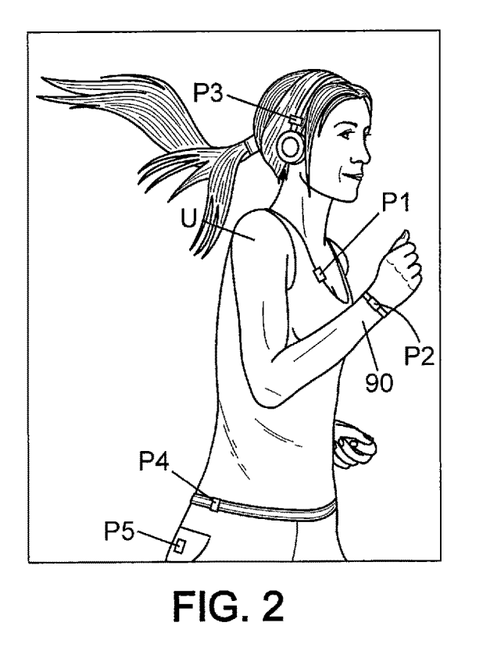
FIG. 2 is a schematic view of a user running, illustrating various possible positions for the device and coupling means.
Figure 3:
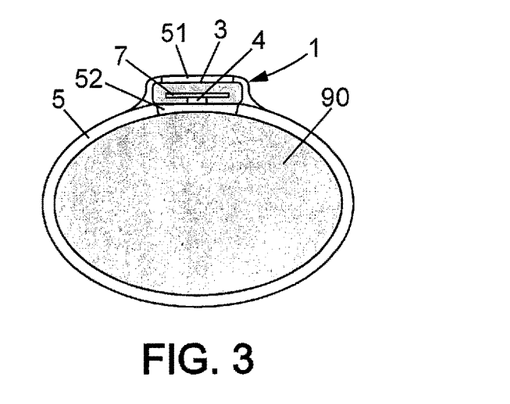
FIG. 3 is a sectional view of a user's wrist.

As illustrated in FIGS. 2-3, the activity monitor 1 is adapted to be coupled to or attached to at least part of the body of the user. For example, the activity monitor 1 may be worn at the belt P4 of the user, or on a fixed bracelet at the wrist P1 of the user, or in the back pocket P5 of the user pant, or around the user waist, or clipped close to the chest P2 of the user, or clipped to a headset equipment P3. The activity monitor could be integrated in a device worn by the user like a headset or a hearing aid.

Advantageously, the activity monitor 1 may be worn at the wrist 90, via a wrist strap 5. Said wrist strap 5 may have a front window 51 through which user can view the display of the activity monitor and a back window 52 that will be discussed later.

A motion sensor 7 is provided in the activity monitor on order to sense the accelerations and movements of the user. The motion sensor is formed in the illustrated example as a multi-axis acceleration sensor 7 (also called 'accelerometer').

The activity monitor may also comprise a temperature sensor 4. In some body locations, the temperature sensor 4 is intended to be close to the body of the user in order to sense an environmental temperature close to the user's skin. For example, illustrated on FIG. 3, the temperature sensor 4 can be located at the back side of the device, opposite to the display 3, and thanks to the back window of the wrist strap 5, the temperature sensor is facing the skin of the user at the user's wrist 90.

Figure 4:
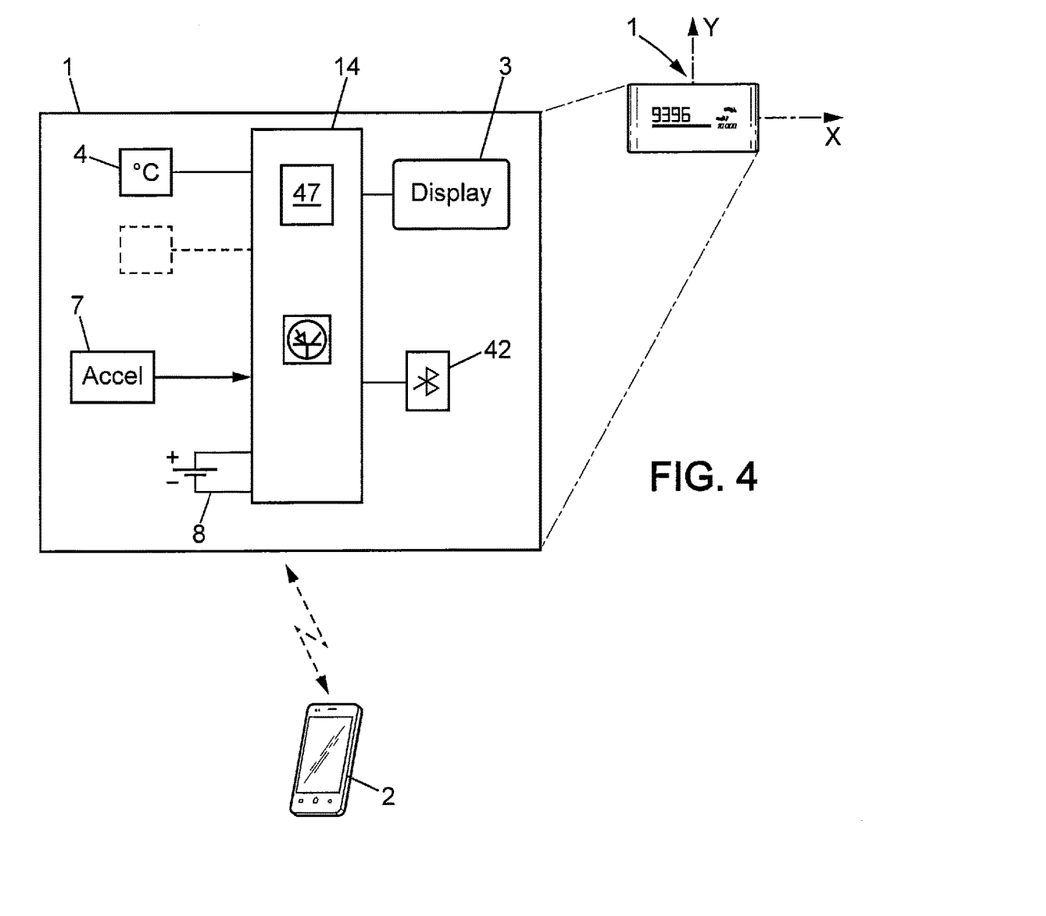
FIG. 4 is a view of a schematic block diagram of the monitoring device.

As illustrated on FIG. 4, the activity monitor 1 may include a processing unit 14 connected to the multi-axis acceleration sensor 7. The processing unit 14 samples the signals outputted by the acceleration sensors. The processing unit 14 computes said signals in order to assess user acceleration, movements and other information as this will be discussed below.

The activity monitor 1 comprises a display 3 controlled by the processing unit 14. On the display, various data or metrics can be made available to the user such as number of steps, stairs climbed, calories burned, etc. . . The monitor may also display if the user is awake or asleep. The totalled metrics could be set to zero daily or on another basis depending on the configuration.

The activity monitor comprises a wireless communication interface 42 (here for example Bluetooth™, or Bluetooth™ Low Energy 'BLE' or the like), for sending collected data to a second device 2 like a smartphone for example.

The activity monitor 1 is powered by an on-board source of energy 8, for example a rechargeable battery. This battery supplies all the on-board elements in the device (the sensor 7, the display 3 and the processing unit 14, etc. .).

The activity monitor 1 also comprises the abovementioned temperature sensor 4, and may also comprise various other sensors 9 like an optical sensor, on On/Off switch, a touch pad area, environmental sensors, pollutants sensors, etc. . .

Figure 5:
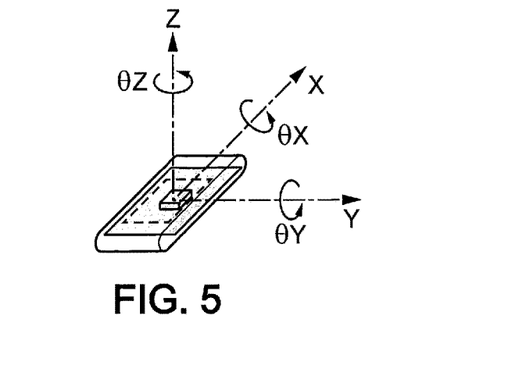
FIG. 5 is a schematic view of a motion sensor included in the monitoring device.

On FIG. 5 the acceleration sensor or accelerometer 7 is represented. In the illustrated example, it's a 6 axes sensor, able to measure linear accelerations along the three perpendicular directions X, Y, Z, and able to measure the rotation motion around the three perpendicular axis X, Y, Z. Miniature gyrometers are used for rotation motions θX, θY, θZ, preferably integrated in a single electronic package.

According to a first advantageous aspect of the invention, the monitoring device is able to recognise the condition when the user wears the monitoring device at the wrist, feature which relies on a counting of the number of the changes of predominant acceleration axis.

Figure 6:
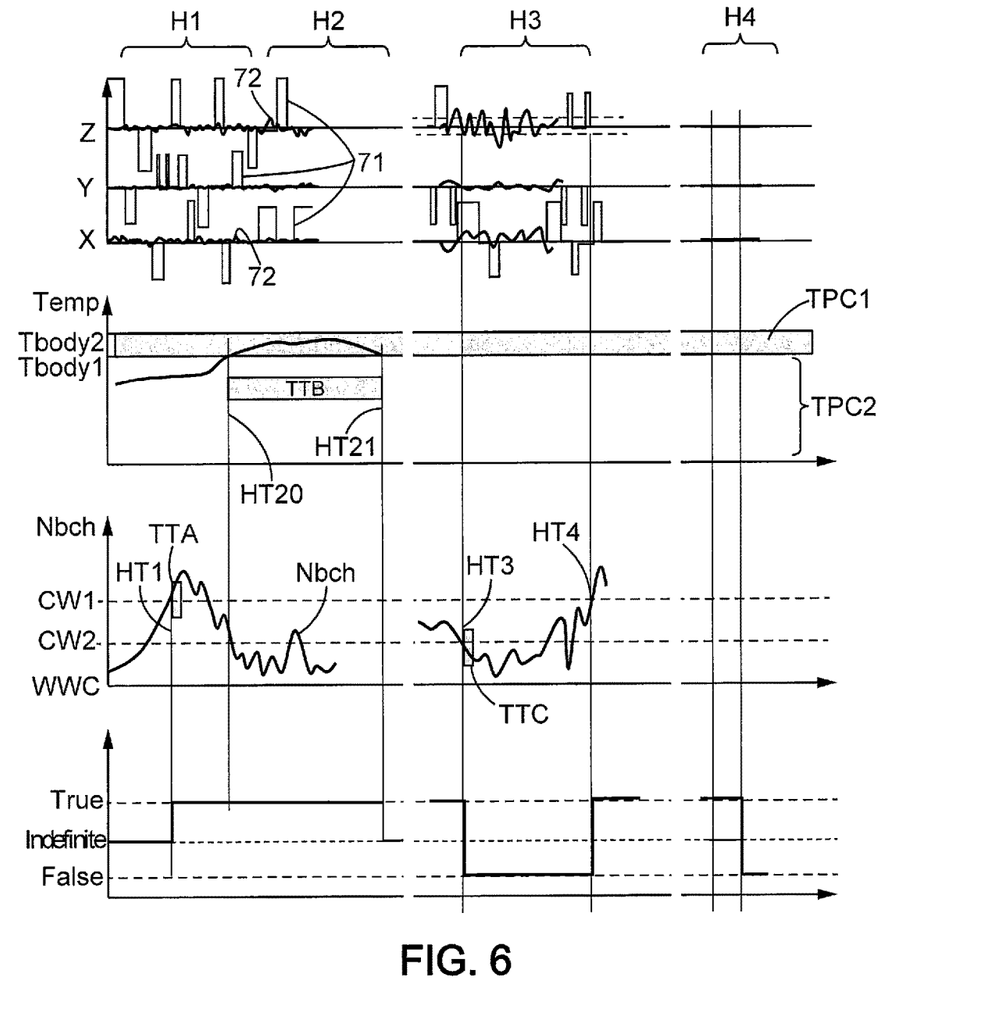
FIG. 6 shows a time chart illustrating the detection of a wrist worn condition.

In other words, data on the changes of predominant acceleration axis of the activity monitor is used to determine if the user is wearing the activity monitor at the wrist or not, as this will be illustrated with the help of FIG. 6.

The predominant axis is defined as the axis along which the acceleration force is the highest. At each instant the monitoring device 1 senses each acceleration axis (X,Y,Z) and determines which one has the highest value, that is to say the predominant axis having the largest acceleration (step 'Wa' of the method).

If the activity monitor is still, only the gravity is sensed by the acceleration sensor; if the activity monitor is moved, the inertia forces are added to the gravity. However, in the case when the monitoring device is worn by a user U, the inertia forces are alternate and the mean value is close to 0 or equal to 0.

Advantageously, the monitoring device senses the 3 linear acceleration signals X,Y,Z, and those signals are filtered by a first low pass filter (analog or digital) having a cutoff frequency at about 3 or 4 Hz in order to discard all electrical disturbances and somewhat high frequency interferences that are not related with user's movements.

Secondly and optionally, a second low pass filter having a cutoff frequency below 0.5 Hz or 0.25 Hz can be applied to determine absolute orientation of the device; such low pass filtering eliminates the acceleration induced by alternate inertia forces due to movements such that the filtered acceleration is substantially equal to gravity. The gravity reliably reflects the absolute orientation of the monitoring device.

It should be noted that since the gravity is higher that most of mean values of X,Y,Z induced by the user's movements, the second low pass filter is not mandatory to determine the predominant axis among X,Y,Z.

As a matter of fact, each of the acceleration signals can be divided into a first component outputted after a low pass filter (named DC component) and a second component called AC component obtained after suppression of the continuous DC component from the raw acceleration signal. The low pass filter can be the second low pass filter or another third low pass filter.

It has been discovered by the inventor(s) that when the monitoring device is worn at the wrist, the changes of orientation are more numerous than in any other position on the body.

Therefore, the monitoring device determines each change of predominant axis when the largest acceleration changes from one axis to another, for example from X to Y, or from Y to Z, or from Z to Y, etc. (step 'Wb' of the method).

Then the monitoring device (the processing unit 14) computes the number of such changes per time period, referred to as Nbch, which is step 'Wc' of the method.

Various methods can be used to output this ratio Nbch, for example a simple one consisting in incrementing a counter at each change of predominant axis and decrementing the same counter as the time passes by (which provides a natural time average filter).

Another method consists in counting the number of changes of predominant axis per period of time. Each period, a new number Nbt is calculated. Optionally, the new outputted number Nbch may be the result of a weighed average of Nbt and the previous value of Nbch. The period of time may be chosen according to various requirements, between 10 seconds and 150 seconds.

Of course other more sophisticated methods to issue a filtered Nbch can be used. Further, the processing unit compares the number of changes of predominant axis per time period Nbch with a stored threshold named first predetermined threshold named CW1.

In the present example, the predetermined threshold CW1 can be 5 changes per minute, or 8 changes per minute, or 10 changes per minute, or 15 changes per minute, or may result from a learning procedure.

If Nbch>CW1, then a 'wrist worn condition' WWC is set to be true, meaning that the activity monitoring device is assumed to be actually worn at the user's wrist. This decision is referred to as step 'Wd' of the method.

Advantageously, the reference time period may be chosen between 30 seconds and 120 seconds. However, any other reference time period could be chosen.

Optionnally, the comparison Nbch>CW1 has to be verified for a first auxiliary time period TTA in order to make the decision WWC being true.

Further, at step Wd—of the method, the abovementioned wrist worn condition can be confirmed by a temperature correlation. More precisely, a predetermined temperature criterion TPC1 is provided; for example, said predetermined temperature criterion TPC1 may be a temperature interval comprised between Tbody1 and Tbody2. If the sensed temperature meets this first predetermined temperature criterion TPC1, comprised between Tbody1 and Tbody2 in the illustrated example, the processing unit can confirm the wrist worn condition.

Therefore, advantageously, the temperature sensor can be used to extend the wrist worn condition over time even if the user does not move substantially, by continuously monitoring the sensed temperature.

More precisely, if the sensed temperature keeps meeting the above-mentioned predetermined temperature criterion TPC1 over a certain period of time TTB (may be called 'second auxiliary predetermined period' TTB), the wrist worn condition can be maintained over said period of time TTB. Thus, even if the wrist stays still, the wrist worn condition can be extended.

Further, the method performed by the processing unit can also determine when the activity monitor 1 is not worn anymore by the user. More precisely, if the number of changes of predominant axis per time period Nbch is below a second predetermined threshold 'CW2', (instantaneously or over a third auxiliary period of time TTC, according to the filtering method relative to Nbch); then the wrist worn condition is assumed to be false.

Advantageously, the second predetermined threshold CW2 is lower than the first predetermined threshold CW1. For example CW2 is equal to 50% of CW1 or preferably 25% of CW1.

Practically, the condition when the wrist worn condition is assumed to be false may correspond to the case when the user U has moved the monitoring device from the wrist to another body location, where linear acceleration is predominant and the direction of gravity relative to the device does not change much; It also corresponds to the case when the user does no wear the device anymore.

It is also to be noted that whenever the acceleration sensor signals exhibits no change at all, that means that the monitoring device is not worn by the user and has been laid down still; in this case too, the wrist worn condition is assumed to be false.

The knowledge of the wrist worn condition helps the monitoring device to compute more accurately the metrics of the various activities undertaken by the user. Appropriate corrections on caloric burn, distance traveled, stairs climbed, etc. can be made when the proper position on the body is known. In the present case, the wrist worn condition is determined, nearly in real time, for the benefits of accurate calculations.

Referring now to FIG. 6, various data are illustrated, the number of changes of predominant axis Nbch, the sensed temperature STemp, the sensed acceleration on the 3 axis X,Y,Z, and the resulting information i.e. the wrist worn condition WWC.

In the first sequence H1, the wrist worn condition WWC is initially indefinite, and the number of changes of predominant axis Nbch is monitored.

XYZ charts exhibit the predominant acceleration axis after the low pass filtering which result in squared signals 71. Also the AC component 72 of each signal X,Y,Z are shown.

At the time HT1, when Nbch exceeds the predetermined threshold CW1, (with or without the time window confirmation TTA), WWC is set to true, regardless of the temperature information and the acceleration information.

The second sequence H2 illustrates the temperature correlation as explained above, between instants HT20 and HT21, the sensed temperature meets the temperature criterion TPC1. In a simple case as illustrated, the temperature criterion TPC1 corresponds to the condition when the temperature is comprised between two temperature thresholds, namely a first predetermined temperature threshold Tbody1 and a second predetermined temperature threshold Tboby2.

If the sensed temperature keeps meeting the temperature criterion TPC1, this allows to maintain the wrist worn condition at true, regardless of the values of Nbch and the acceleration information.

In the present example, the first and second predetermined thresholds Tbody1 and Tboby2 can be respectively 25° C. and 35° C., but of course other values can be considered, and those threshold values may result from a learning procedure.

It should be noted that a second temperature criterion TPC2 is defined, the use of which will be detailed below.

The third sequence H3 illustrates a sequence when WWC becomes false on a condition of the value of Nbch becoming sufficiently low.

At instant HT3, Nbch becomes lower than the second predetermined threshold CW2, and therefore the processing unit assumes that the monitoring device is worn at a body position different from the wrist position (wwc is set to False). Optionally, the Nbch<CW2 condition has to be verified along the TTC time window (relative to the above mentioned third auxiliary predetermined time period).

At instant HT4, Nbch becomes again higher than CW1 and the condition WWC is set to true again.

The fourth sequence H4 illustrates a sequence when WWC becomes false on a condition that the monitoring device is laid down and not worn by the user. In this particular case, the AC component of the three accelerometers are null. Thus the processing unit sets WWC to 'False'.

It should be noted that it is not excluded to use the girometer data, namely rotation motions θX, θY, θZ, to compute a change of orientation ratio.

Besides, it should be noted that the method explained above can also be used to detect more generally that the monitoring device is worn at an extremity of the user's body. More precisely, the method similar to the one used for the wrist position can be used to detect that the monitoring device is worn at the foot of the user. The number of changes of orientation per period of time is computed similarly, different thresholds CW1 CW2 are used (preferably lower values), and this is combined with the level of the linear acceleration signals which have a different pattern when the monitoring device is worn at the foot (higher peak values).

According to a second advantageous aspect of the invention, the monitoring device is able to recognise various type of user's activities, including sleep.

Indeed, the monitoring device is intended to monitor all the phases of the user's life, including rest and sleep, and to report to the user the duration of sleep, quality of sleep etc.

The accelerometer data is collected continuously by the processing unit 14 of the monitoring device 1. As already explained, the acceleration signals can be divided into a first component outputed after the low pass filter and a second component called AC component after suppression of the continuous DC component. In the following, we focus on the AC components. Each linear AC component can be time-averaged with a rolling average window.

Since the motion sensor is formed as a 3-axis accelerometer (X,Y,Z) the current sensed level of activity AL is determined by summing the average signals of the 3 linear accelerometers, in particular AC components for each linear direction (step 'Sa' of the method).

Figure 8:
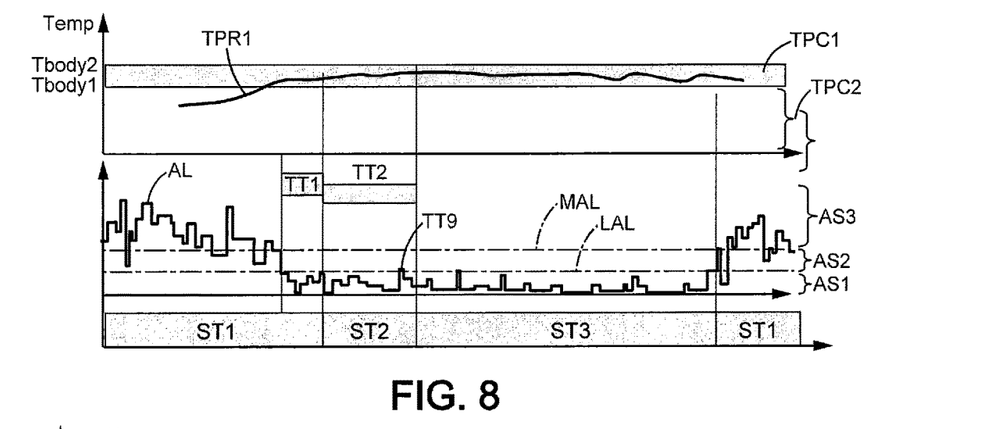
FIG. 8 shows a general time chart illustrating a sleep condition detection.
Figure 9:
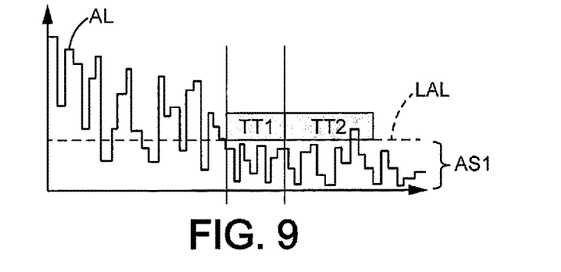
FIG. 9 is analogous to FIG. 8 and shows a more detailed time chart illustrating a sleep condition detection.

Three activity standards are defined: a low standard of activity (AS1), a medium standard of activity (AS2) and a high standard of activity (AS3). Those levels of activity are defined by two thresholds: LAL (predefined low level of activity) and MAL (predefined medium level of activity), as shown in FIG. 8.

Besides the definition of the levels of activities, the monitoring device also defines 4 states (ST1: AWAKE, ST2: POTENTIAL_SLEEPING, ST3: SLEEPING, ST4: NOT WORN) that will be detailed below, referring to FIG. 7. The state chart illustrated in FIG. 7 comprises boxes that represent states (ST1-ST4) and arrows CXY that represent logical conditions of transition from one state to another.

Figure 7:
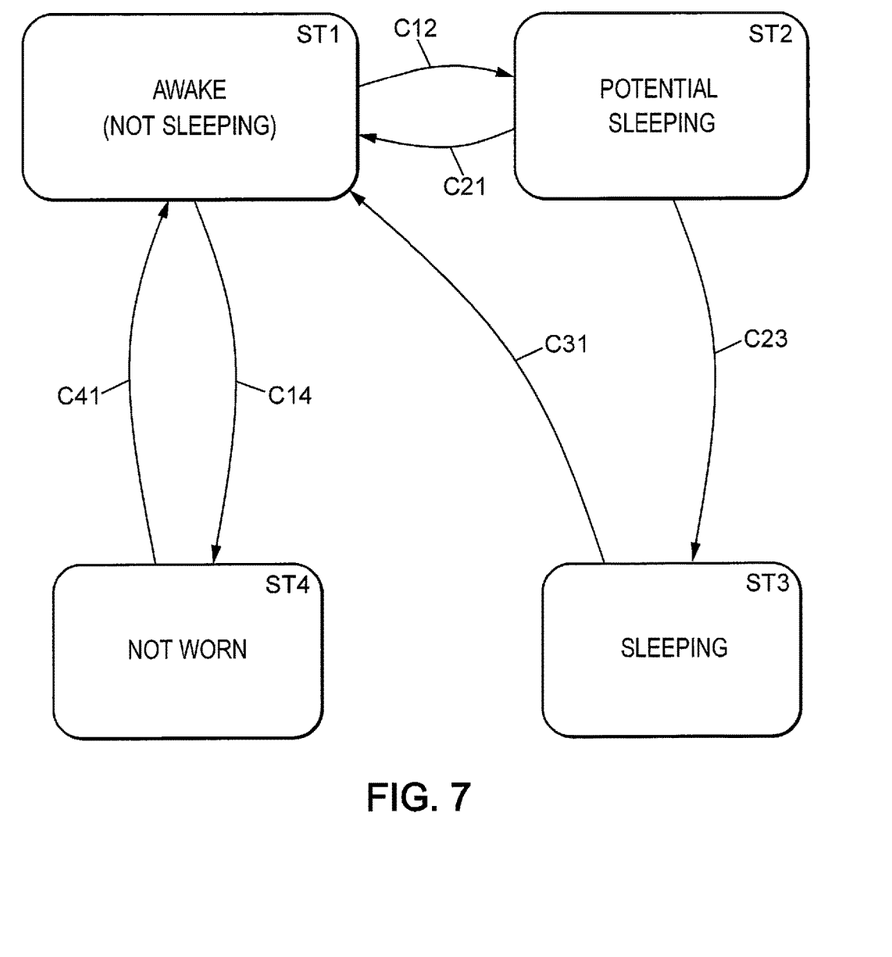
FIG. 7 shows state chart illustrating the behaviour of the monitoring device.

Under another perspective, the activity monitor 1 determines via the temperature sensor 4 a current temperature (T) and a first temperature profile (TPR1) over time (step 'Sb' of the method).

The temperature measurement gives complementary information to corroborate acceleration data, as explained below.

If the sensed level of activity is below the predefined low level of activity (LAL) for at least a first period of time T1, a state 'POTENTIAL_SLEEP' is assumed.

It may be complemented by one of the two following conditions: if the first temperature profile TPR1 meets a first predetermined temperature criterion TPC1 over the first period of time TT1, then a state 'POTENTIAL_SLEEP' is confirmed.

Or, if the first temperature profile TPR1 meets first predetermined temperature criterion TPC1 over the second period of time TT2 then a state 'SLEEPING' ST3 is confirmed.

Advantageously, the second period of time TT2 starts as soon as a state 'POTENTIAL_SLEEP' is assumed or confirmed. Of course, if too much activity is sensed during this period, transition C21 as explained below is activated, and the current state becomes again AWAKE ST1.

If the user wears the activity monitor (wrist or elsewhere) the sensed temperature profile is expected to meet the first predetermined temperature criterion TPC1. For example the temperature could be included in the interval Tbody1 and Tbody2.

If the user doesn't wear the activity monitor 1, the detected temperature would be lower than Tbody1. Tbody1 can be set to 25° C. or similar value.

Figure 10A:
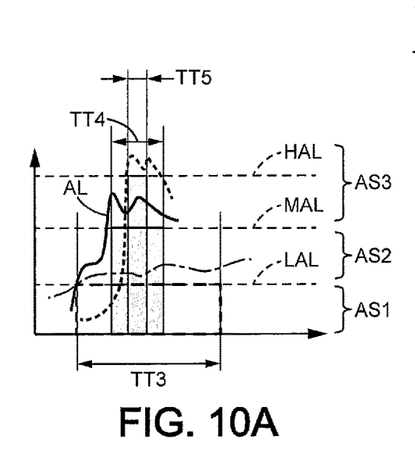
FIGS. 10A and 10B are analogous to FIG. 8 and show more detailed time charts illustrating an awakening condition detection.

Turning now to FIG. 7, to begin with, any important detected movement over a certain time results in the assumption of state ST1 AWAKE, this is illustrated by transitions C21, C31, C41, and shown by FIG. 10A.

Transition C14 (AWAKE to NOT WORN) is assumed when no movement is detected and the temperature meets the second predetermined temperature criterion TPC2. This means the activity monitor lies still somewhere and is not worn.

This second predetermined temperature criterion TPC2 may consist in a simple temperature condition namely STemp<Tbody1, or any other threshold value different from Tbody1, this threshold being advantageously set to 22° C. or 23° C. or 24° C. Alternatively, the second predetermined temperature criterion TPC2 may also include a condition on temperature change (see below).

Transition C12 (AWAKE to POTENTIAL_SLEEP) is assumed when the sensed level of activity is below the predefined low level of activity (LAL) for at least a first period of time TT1, and if the sensed temperature meets the first temperature criterion TPC1 (here between Tbody1 and Tbody2).

Transition C23 (POTENTIAL_SLEEP to SLEEPING) is assumed when the sensed level of activity does not exceed another predefined level of activity (for example MAL)

more than another predefined period of time T2, and if the sensed temperature keeps meeting the first temperature criterion TPC1 (here between Tbody1 and Tbody2).

Whenever the transition C23 becomes true, the data recorded in the state ST2 are confirmed to be effective sleep. In contrary, whenever the transition C21 terminates the ST2: POTENTIAL_SLEEP, the data recorded in that state ST2 is not considered to be effective sleep.

Therefore, whenever the transition C23 becomes true, the instant considered to be the moment when the user fell asleep is the previous time of transition C12 (the ST2 is considered a posteriori to be effective sleep).

Also, the instant considered to be the moment when the user emerges from sleep is the next transition C31.

Therefore, the processing unit 14 is able to accurately calculate the duration of sleep between the above-mentioned transitions C12 and C31, (provided that ST2 was followed directly by ST3 (C23)).

Of course total duration of sleep for one night is calculated as the concatenation of several sleep phases whenever the user awoke once or more during the night.

It should be noted that, during states ST2 and ST3, whenever a movement resulting in a level of activity above the predefined low level LAL, as illustrated at instant TT9, this does not result in exiting the current state.

Figure 10B:
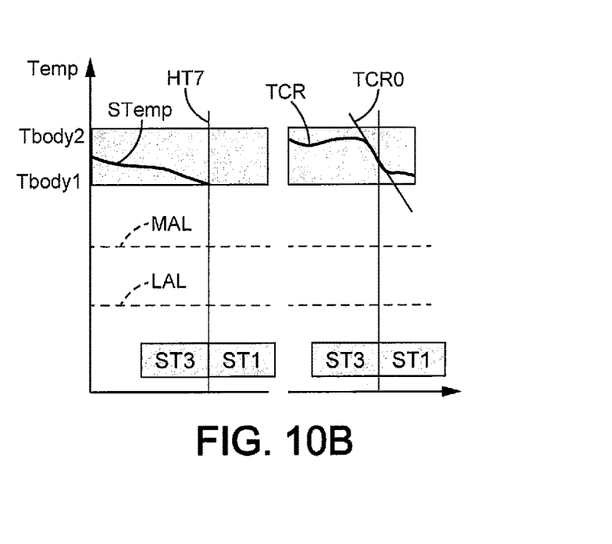

Transition C31 (referred to as 'wake activity criterion') is now explained in more details, referring to FIGS. 10A and 10B. The processing unit will decide an end of the sleeping phase (SLEEPING to AWAKE) according to different possible conditions, based on a certain activity level AL or on a sensed temperature condition STemp.

One of the condition is that the sensed level of activity AL is above the predefined low level of activity LAL for at least a third period of time TT3.

Another condition can be that the sensed level of activity is above a medium level of activity MAL for at least a fourth period of time TT4.

Still another condition can be that the sensed level of activity is above a high level of activity HAL for at least another, short, period of time TT5, let's say several seconds or more.

Yet another condition relates to the sensed temperature; the wake activity criterion will be met if the sensed temperature meets the already mentioned second predetermined temperature criterion TPC2.

This second predetermined temperature criterion TPC2 may consist in a simple temperature condition namely STemp<Tbody1, or any other threshold value different from Tbody1, this threshold being advantageously set to 23° C. or 24° C. or 25° C.

This is shown on FIG. 10B at instant HT7.

Alternatively, the second predetermined temperature criterion TPC2 may also include a condition on temperature change. More precisely, the processing unit calculates a ratio of change of sensed temperature per time unit TCR, and the wake activity criterion also comprises a condition in which said ratio of change of sensed temperature per time unit exceeds a predefined temperature change threshold TCR0. Additionally, the absolute temperature condition can be combined with the above mentioned condition on temperature change. For example, conditions TCR>TCR0 and STemp<TTH0 can be combined, with TTH0 set to 26° C.

Regarding transition C21, it includes conditions already explained for transition C31, but also conditions on temperature. For example if POTENTIAL_SLEEP (ST2) is the current state, and the current temperature profile is being monitored, two cases may arise:

if current temperature profile meets the criterion TPC1, then user is considered to be in the sleeping state ST3 as already explained, but, if the current temperature profile does not meet the criterion TPC1, then user is considered still awake (transition C21 activates).

Thanks to the monitoring of the temperature, and according to the fifth aspect of the present invention, it is disclosed a method to determine that the user is awake with a very low level of activity. Advantageously, this allows to distinguish a sleep state of the user from a very low active but still awake state. More precisely, if the user is sitting on a sofa watching TV, then the level of activity will be below the predefined low level of activity LAL, however, the temperature profile will probably not meet the first temperature criterion TPC1. Furthermore, this little active awake state can be confirmed by data that are coming from other auxiliary devices. It should be noted that when the user goes to sleep, the most likely the position for the monitoring device is the wrist position, and therefore the temperature information mostly reflects the skin temperature.

According to the third aspect of the present invention, the proposed method is configured to determine a current coupling position of the monitoring device on the user's body among a plurality of possible body coupling positions. Said plurality of possible body coupling positions includes extremities (hand, wrist, foot), upper arm, upper leg, hip, waist, torso, neck, head.

The method comprises the steps of collecting the accelerometer signals, analysing time and frequency characteristics of the collected signals, comparing said characteristics to predefined patterns, and then deciding the most likely body coupling position.

Preferably the plurality of possible body coupling positions includes extremities (hand, wrist, foot), upper arm, upper leg, hip, waist, torso, neck, head. The predefined patterns may include criteria or thresholds on the following items: predominant frequency, frequency of orientation changes, amplitude, symmetry or the symmetry versus arrange value, etc.

Hip coupling position will be assumed (decided to be the most likely) if acceleration module (sum of 3 axis linear acceleration signals) is dissymmetric from one step to another, and the average level is crossed at each step.

Neck and/or head coupling position will be assumed if acceleration module is symmetric from one step to another (sinus like), and the average level is crossed at each step.

Wrist and/or foot coupling position will be assumed if the acceleration axis which is mostly vertically oriented is frequently changing (see details in the patent).

Upper arm and/or upper leg coupling position will be assumed if the acceleration axis which is mostly vertically oriented is changing but less frequently than on the wrist.

According to a variant of the third aspect of the present invention, the proposed method is configured to determine, using also the temperature signal, on the one hand a current coupling position of the monitoring device on the user's body among a plurality of possible body coupling positions and to concurrently determine on the other hand the current type of activity undertaken by the user among a plurality of possible activities.

The plurality of possible body coupling positions are the same as above, whereas the plurality of possible user's activities may include sleeping, walking, running, cycling, swimming, golfing, doing racket sport, etc. .

The predefined patterns may include criteria or thresholds, with acceleration and temperature signal correlation, on the one hand acceleration signals such as predominant frequency, frequency of orientation changes, amplitude, symmetry or the symmetry versus average value, etc, and the other hand predefined temperature thresholds regarding temperature signal.

A detailed decision matrix is given in Table 1 at the end of the present specification, it is to be noted that the content of said Table 1 is non-limiting. In this table, cross conditions correlating acceleration signals and temperature signals allows the monitoring unit to infer both the current position of the monitoring device and the current activity of the user.

According to a fourth aspect of the present invention, the proposed method is configured to correlate data from various external devices, besides the already mentioned communication with a smart phone 2. More precisely, the monitoring device 1 can exchange data with various external devices (in particular receive from) through the short-range wireless communication interface. More precisely other devices located in the same room or in the vicinity of the monitoring device can send additional information to the monitoring device 1 in order to make the decision on the body coupling position and/or on the user activity faster and more reliable.

Said various external devices may include the following devices:

an air quality sensor (for example CO2 or VOC sensor), which is useful to recognize and/or confirm the sleep activity, knowing that CO2/VOC level in a room is directly correlated with number of people in a room; a strong increase of CO2/VOC level in the bedroom (>200 ppm) shows presence of one person, a second increase shows presence of a second person . . . Inversely a strong decrease in CO2/VOC level means that the door was opened and someone left the room; hence if the CO2/VOC level is below a 1 person level, therefore this confirms the awakening of the user, a sleep sensor arranged on a bed (pneumatic, piezoelectric, sound, video), which is also useful to recognize and/or confirm the sleep activity, since such sleep sensor allows to detect somebody standing up from bed, noise, movement of the user in bed; if the sleep sensor senses nobody in the bed this confirms the awakening of the user;

a geo-location sensor, such as GPS, (housed on a smartphone, smartwatch or something similar), which is useful to recognize and/or confirm running and/or sport activity, since said geo-location sensor is able to provide accurate location and travel speed, an image/video apparatus, such as a home video monitoring system, said video system being able to analyze the captured images, in particular images of the user, and spot the location and position of the activity monitoring device on the user, and transmit the related data, a weighing scale with user detection, which is useful to determine a wake-up condition of the user, since if the user is detected on the scale, the user is awake.

Thanks to the above methods, the knowledge of the current coupling position of the monitoring device on the user's body and the knowledge activity undertaken by the user allows the monitoring device to improve the accuracy of the calculation regarding number of steps, caloric burning, travelled distance, etc. . .

TABLE 1

| When worn on the torso | | |
| --- | --- | --- |
| sleep | Activity level scores (see specification above) | High temperature (above threshold TTH3) |
| walk (including golf and any sport where walking is needed) | Sequence of max and min in the 3 axis acceleration module signal, below adequate frequency threshold FTH1, above adequate amplitude threshold ATH1 | Any temperature (not relevant) |
| run (including any sports where running is needed) | Sequence of max and min in the 3 axis module signal, above adequate frequency threshold FTH2, above adequate amplitude threshold ATH2 | Any temperature (not relevant) |
| cycle | Random high frequency acceleration module | Not relevant |
| when worn at the extremities | | |
| sleep | Same than sleep/torso case above, | High temperature (above threshold TTH3) |
| walk | Same than walk/torso case above in Table1, with different amplitude threshold | May be used to confirm a decision |
| run | Same than run/torso case above in Table1, with different amplitude threshold | temperature increase increases likelihood (but is not mandatory) |
| swim | The acceleration axis which is mostly vertically oriented is changing with a relatively fixed period | Any temperature (not relevant) |
| cycle | Same than cycle/torso case with higher amplitude acceleration module | Any temperature (not relevant) |
| racket sport | The acceleration axis which is mostly vertically oriented is changing frequently, on a non regular basis and acceleration amplitude is high (above a given threshold) | temperature increase increases likelihood (but is not mandatory) |
| golf | acceleration caracteristic pattern of swing recognized by machine learning, separated by short walking period | Any temperature (not relevant) |

The invention claimed is:

1. A personal activity monitor wearable by a user, such personal activity monitor comprising a motion sensor formed as an at least 3-axis accelerometer for providing acceleration signals, defining a first local spatial reference with same axis associated with the motion sensor and independent from a spatial geographical reference, and a processor unit, wherein the personal activity monitor may be worn by the user at various body locations, and configured to determine that the device is worn at the wrist location among other possible body locations,
wherein the personal activity monitor is further configured to:
   apply a low pass filter to the acceleration signals, with a cut-off frequency less than 0.5 Hz, wherein such low pass filtering eliminates the acceleration induced by alternate inertia forces due to movements and keep only the DC component of the acceleration signals such that the filtered acceleration is substantially equal to gravity, reflecting an absolute orientation of the personal activity monitor,
   Wa—identify at each instant which axis of the first local spatial reference senses the largest acceleration, the largest acceleration being provided by gravity,
   Wb—determine a change of predominant axis when the largest acceleration changes from one axis to another in the first local spatial reference,
   Wc—determine a number of changes of predominant axis per time period,
   Wd—define a wrist worn condition, meaning that the personal activity monitor is worn at the wrist of the user, and,
infer that the wrist worn condition is true, based on a determination that the number of changes of predominant axis per time period exceeds a first predetermined threshold,
   We—, infer that the wrist worn condition is or has become false, based on a determination that the number of changes of predominant axis per time period is below a second predetermined threshold; and
thereby, determine that the personal activity monitor is worn or is not worn at the wrist of the user, meaning that the personal activity monitor is worn at a body location different from a wrist or not worn at all.

2. The personal activity monitor of claim 1, wherein acceleration signals consists of 3 linear acceleration signals.

3. The personal activity monitor of claim 1, wherein the second predetermined threshold is lower than the first predetermined threshold.

4. The personal activity monitor of claim 1, wherein the number of changes of predominant axis is computed periodically over the last elapsed time period.

5. The personal activity monitor of claim 1, further comprising a temperature sensor enclosed in the personal activity monitor, wherein in step
   Wd—, the wrist worn condition is maintained over a certain period of time based on a temperature sensed by the temperature sensor meeting a first predetermined temperature criterion over said certain period of time.

6. The personal activity monitor according to claim 5, in which the first predetermined temperature criterion is a temperature interval comprised between a first predefined temperature threshold and a second predefined temperature threshold.

7. A personal activity monitor, comprising a motion sensor, a processor unit and a temperature sensor, wherein a set of at least three states are defined regarding the personal activity monitor together with the user, the set of states comprising at least NOT WORN, WORN&AWAKE, WORN&POTENTIAL SLEEPING, WORN&SLEEPING, the personal activity monitor being configured to:
   Sa—determine continuously via the motion sensor a current level of activity, and compare the current level of activity to a predefined low level of activity, and to a second predefined level of activity,
   Sb—determine via the temperature sensor a current temperature at the vicinity of the activity monitor, and a first temperature profile,
   Sc—determine that the personal activity monitor is being worn by the user has entered a WORN POTENTIAL SLEEPING state, based on a determination that the current level of activity is below the predefined low level of activity for at least a first period of time and concurrently that the first temperature profile meets a first predetermined temperature criterion over the first period of time
   based on a determination that the current level of activity remains below the second predefined level of activity and concurrently that the first temperature profile keeps meeting the first predetermined temperature criterion over a second period of time, determine that the personal activity monitor is being worn by the user and has entered a WORN&SLEEPING state, and then include a duration of the WORN&POTENTIAL SLEEPING state into effective sleep, and otherwise exclude the duration of the WORN&POTENTIAL SLEEPING state from effective sleep count,
   Sd—determine that the user has emerged from sleep, based on a first condition at least requiring that the current level of activity is above the predefined low level of activity for at least a third period of time,
   Se—determine that the user has emerged from sleep, based on a second condition at least requiring that the current level of activity is above the second predefined level of activity for at least a fourth period of time, and
   Sf—calculate a sleep duration of the user, between instants of entering and emerging from sleep,
   calculate a total sleep duration as the addition of several consecutive sleep phases.

8. The personal activity monitor according to claim 7, wherein the first condition and/or the second condition further requires that the current temperature meets a second predetermined temperature criterion met when the current temperature is below a first predefined temperature threshold.

9. The personal activity monitor according to claim 8, wherein the third predefined level of activity is greater than the predefined second level of activity which is greater than the predefined low level of activity; and
   wherein the third period of time is greater than the fourth period of time which is also greater than the fifth period of time.

10. The personal activity monitor according to claim 7, wherein the first predetermined temperature criterion is a temperature interval comprised between a first predefined temperature threshold and a second predefined temperature threshold.

11. The personal activity monitor according to claim 10, wherein the processing unit is further configured to calculate a ratio of change of sensed temperature per time unit, and wherein the first condition and/or the second condition further requires that said ratio of change of sensed temperature per time unit exceeds a predefined temperature change threshold.

12. The personal activity monitor according to claim 7, wherein the motion sensor is formed as a 3-axis accelerometer configured to provide raw acceleration signals, wherein each of the acceleration signals are divided into a first, DC component outputted after a low pass filter and a second, AC component obtained after suppression of the first DC component from the raw acceleration signals, and the current level of activity is determined by summing the average signals of the AC components of each of the 3 linear acceleration signals.

13. The personal activity monitor according to claim 7, wherein the second predefined level of activity is greater than the predefined low level of activity, and
   wherein the third period of time is, greater than the fourth period of time.

14. The personal activity monitor according to claim 7, further configured to:
   determine that the user has emerged from sleep, based on a third condition at least requiring that the current level of activity is above a third predefined level of activity for at least a fifth period of time.

\* \* \* \* \*